(12) United States Patent  
    Wiederhold et al.

(10) Patent No.:    US 12,577,218 B2  
(45) Date of Patent:     Mar. 17, 2026

(54) METHOD FOR INCREASING PROPYLENE OXIDE OUTPUT OF AN INTEGRATED PROCESS FOR MAKING PROPYLENE OXIDE AND PROPYLENE GLYCOL

(71) Applicant: Evonik Operations GmbH, Essen (DE)

(72) Inventors: Holger Wiederhold, Darmstadt (DE); David Bolz, Frankfurt (DE); Bernd Jaeger, Bickenbach (DE)

(73) Assignee: Evonik Operations GmbH, Essen (DE)

( * ) Notice: Subject to any disclaimer, the term of this patent is extended or adjusted under 35 U.S.C. 154(b) by 559 days.

(21) Appl. No.: 18/249,584

(22) PCT Filed: Oct. 7, 2021

(86) PCT No.: PCT/EP2021/077754

§ 371 (c)(1),  
(2) Date: Apr. 19, 2023

(87) PCT Pub. No.: WO2022/084060

PCT Pub. Date: Apr. 28, 2022

(65)           Prior Publication Data

US 2023/0382878 A1      Nov. 30, 2023

(30)       Foreign Application Priority Data

Oct. 21, 2020    (EP) .................................... 20202983

(51) Int. Cl.  
   *C07D 301/19*       (2006.01)  
   *C07D 301/12*       (2006.01)  
   *C07D 301/32*       (2006.01)

(52) U.S. Cl.  
   CPC ......... *C07D 301/19* (2013.01); *C07D 301/12* (2013.01); *C07D 301/32* (2013.01)

(58) Field of Classification Search  
   CPC .................................................... C07D 301/19  
   See application file for complete search history.

(56)          References Cited

U.S. PATENT DOCUMENTS

| | | |
|---|---|---|
| 10,214,471 B2 | 2/2019 | Wiederhold et al. |
| 2006/0025637 A1 | 2/2006 | Babler et al. |
| 2018/0354878 A1 | 12/2018 | Wiederhold et al. |

FOREIGN PATENT DOCUMENTS

| | | |
|---|---|---|
| CN | 1678598 | 10/2005 |
| CN | 1304384 C | 3/2007 |
| CN | 108779053 | 11/2018 |
| WO | 2017/089075 | 6/2017 |
| | 10214471 | |

OTHER PUBLICATIONS

Zheng Wei, "Production status and market trends of propylene oxide/propylene glycol", Petrochemical Dynamics, No. 2, 1994, 14 pages with English translation.  
International Search Report dated Feb. 1, 2022, in PCT/EP2021/077754, 5 pages.  
Written Opinion dated Feb. 1, 2022, in PCT/EP2021/077754, 7 pages.  
U.S. Appl. No. 18/249,984, filed Apr. 21, 2023, Wiederhold et al.  
U.S. Appl. No. 18/249,724, filed Apr. 19, 2023, Wiederhold et al.  
U.S. Appl. No. 18/249,980, filed Apr. 21, 2023, Wiederhold et al.  
U.S. Appl. No. 18/249,695, filed Apr. 19, 2023, Wiederhold et al.  
U.S. Appl. No. 18/249,729, filed Apr. 19, 2023, Bolz et al.  
U.S. Appl. No. 18/249,908, filed Apr. 20, 2023, Wiederhold et al.  
U.S. Appl. No. 18/249,982, filed Apr. 21, 2023, Wiederhold et al.  
U.S. Appl. No. 18/249,660, filed Apr. 19, 2023, Wiederhold et al.  
U.S. Appl. No. 18/249,906, filed Apr. 20, 2023, Wiederhold et al.  
U.S. Appl. No. 18/249,825, filed Apr. 20, 2023, Wiederhold et al.  
U.S. Pat. No. 10,214,417, filed Feb. 26, 2019, 2018/0354878, Wiederhold et al.

*Primary Examiner* — John S Kenyon

(74) *Attorney, Agent, or Firm* — Grüneberg Global IP, PLLC

(57)              ABSTRACT

An integrated process for making propylene oxide and propylene glycol involves reacting propene with an oxidant to provide propylene oxide, reacting a fraction of the propylene oxide with water to provide an aqueous glycol solution containing monopropylene glycol and dipropylene glycol, and separating monopropylene glycol and dipropylene glycol from the glycol solution by a multi-step distillation. The propylene oxide output can be increased without increasing capacity of the unit for reacting propene to propylene oxide, by reacting propene and hydrogen peroxide in the presence of a catalyst mixture, containing a phase transfer catalyst and a heteropolytungstate, in a liquid reaction mixture which contains an aqueous phase with a maximum apparent pH of 6 and an organic phase. The reaction mixture is separated into an organic phase, which is recycled to the reaction, and an aqueous phase containing monopropylene glycol and dipropylene glycol, which is passed to replace the glycol solution.

5 Claims, No Drawings

METHOD FOR INCREASING PROPYLENE OXIDE OUTPUT OF AN INTEGRATED PROCESS FOR MAKING PROPYLENE OXIDE AND PROPYLENE GLYCOL

CROSS-REFERENCE TO RELATED APPLICATIONS

This application is the National Stage entry under § 371 of International Application No. PCT/EP2021/077754, filed on Oct. 7, 2021, and which claims the benefit of priority to European Application No. 20202983.1, filed on Oct. 21, 2020. The content of each of these applications is hereby incorporated by reference in its entirety.

BACKGROUND OF THE INVENTION

Field of the Invention

The invention is directed at increasing propylene oxide output of an existing integrated process for making propylene oxide and propylene glycol.

Description of Related Art

Propylene glycol is an important chemical product and is typically produced by reacting propylene oxide with water. Since propylene oxide is a hazardous chemical, production of propylene glycol is typically integrated on the same production site with a process for making propylene oxide to avoid transporting the propylene oxide used for making propylene glycol. Industrial production of propylene glycol is therefore typically carried out by an integrated process which comprises a first step of reacting propene with an oxidant to provide propylene oxide, a second step of reacting a part of the propylene oxide produced in the first step with water to a reaction mixture containing propylene glycols and a third step of separating monopropylene glycol and dipropylene glycol from the reaction mixture of the second step by a multi-step distillation.

The commercial processes for making propylene oxide use either chlorine, an organic hydroperoxide or hydrogen peroxide as the oxidant. When chlorine or an organic hydroperoxide is used as oxidant, the production of propylene oxide must be integrated with a unit for producing the oxidant to prevent transport of chlorine or the organic hydroperoxide. When an organic hydroperoxide is used as the oxidant, the production of propylene oxide is typically integrated with a further unit which converts the alcohol formed from the hydroperoxide to a marketable product. When tert-butyl hydroperoxide is used as the oxidant, the tert-butanol formed from the hydroperoxide is typically further reacted to tert-butyl methyl ether (MTBE). When ethylbenzene hydroperoxide is used as the oxidant, the 1-phenylethanol formed from the hydroperoxide is typically further reacted to styrene. The commercial processes making propylene oxide by reacting propene with hydrogen peroxide typically use a zeolite catalyst and require the use of a solvent which must be separated from the reaction mixture and recycled.

Increasing the production capacity of the commercial processes for making propylene oxide therefore not only requires increasing the capacity of the reaction unit for reacting propene with the oxidant, but also requires a substantial amount of additional equipment. When chlorine or an organic hydroperoxide is used as oxidant, additional equipment is needed for increasing the capacity for producing the oxidant. When an organic hydroperoxide is used with conversion of the resulting alcohol to a marketable product, additional equipment is needed for further reacting the alcohol formed from the hydroperoxide. When hydrogen peroxide is used as oxidant, additional equipment is needed for solvent separation which also leads to increased energy consumption for solvent separation.

WO 2017/089075 discloses a method for producing 1,2-propanediol from propene and hydrogen peroxide comprising: a) reacting propene with hydrogen peroxide in the presence of a catalyst mixture comprising a phase transfer catalyst and a heteropolytungstate, wherein the reaction is carried out in a liquid mixture comprising an aqueous phase with a maximum pH of 6 and an organic phase, b) dividing the two-phase mixture from step a) into an aqueous phase and an organic phase containing propylene oxide, c) returning the propylene oxide contained in the separated organic phase into the reaction from step a) and d) separating 1,2-propanediol from the aqueous phase separated in step b).

SUMMARY OF THE INVENTION

The inventors of the present invention have now found a way for increasing the propylene oxide output of an integrated process for making propylene oxide and propylene glycol which provides additional propylene oxide for sale without increasing the capacity of the unit for reacting propene to propylene oxide and of the units associated with this reaction unit. Such increase of propylene oxide output for sale can be achieved by installing a new unit for reacting propene and hydrogen peroxide to directly provide a solution containing propylene glycols, which solution can be separated to give monopropylene glycol and dipropylene glycol in the existing unit used for separating the reaction mixture provided by reacting propylene oxide with water. The amount of propylene oxide fed to the unit for reacting propylene oxide with water can then be reduced accordingly without losing capacity for producing propylene glycols and the propylene oxide no longer needed for reacting with water becomes available for sale.

Subject of the invention is therefore a method for increasing propylene oxide output of an existing integrated process for making propylene oxide and propylene glycol, the integrated process comprising a step a) of reacting propene with an oxidant to provide propylene oxide, a step b) of reacting a fraction of the propylene oxide provided in step a) with water to provide an aqueous glycol solution comprising monopropylene glycol and dipropylene glycol and a step c) of separating monopropylene glycol and dipropylene glycol from said aqueous glycol solution by a multi-step distillation, said method comprising adding a step d) of reacting propene and hydrogen peroxide in the presence of a catalyst mixture comprising a phase transfer catalyst and a heteropolytungstate in a liquid reaction mixture, comprising an aqueous phase with a maximum apparent pH of 6 and an organic phase, and a step e) of separating the liquid reaction mixture provided by step d) into an organic phase, which is recycled to step d), and an aqueous phase comprising monopropylene glycol and dipropylene glycol, which is passed to step c), where the aqueous phase provided by step e) replaces aqueous glycol solution provided by step b) and at the same time the fraction of propylene oxide passed from step a) to step b) is reduced to lower the output of aqueous glycol solution from step b).

DETAILED DESCRIPTION OF THE INVENTION

In the method of the invention, an existing integrated process for making propylene oxide and propylene glycol is modified for increasing propylene oxide output for commercial sale. The existing integrated process comprises a step a) of reacting propene with an oxidant to provide propylene oxide, a consecutive step b) of reacting a fraction of the propylene oxide provided in step a) with water to provide an aqueous glycol solution comprising monopropylene glycol and dipropylene glycol and a step c) of separating monopropylene glycol and dipropylene glycol from said aqueous glycol solution by a multi-step distillation.

Step a) of the existing process may use any known process for making propene oxide by reacting propene with an oxidant.

Step a) may be a chlorohydrin process where propene is reacted with chlorine to give propylene chlorohydrin intermediates which are then dehydrochlorinated with sodium hydroxide or calcium hydroxide to provide propylene oxide. Suitable chlorohydrin processes are known from the prior art and are described in Ullmann's Encyclopedia of Industrial Chemistry, online edition, entry "Propylene Oxide", pages 5-10, DOI 10.1002/14356007.a22_239.pub3.

Alternatively, step a) may be a hydroperoxide process where propene is reacted with an organic hydroperoxide such as tert-butyl hydroperoxide, ethylbenzene hydroperoxide or cumene hydroperoxide. Suitable hydroperoxide processes are known from the prior art and are described in Ullmann's Encyclopedia of Industrial Chemistry, online edition, entry "Propylene Oxide", pages 1116, DOI 10.1002/14356007.a22_239.pub3. Preferably, the hydroperoxide process uses tert-butyl hydroperoxide and the integrated process produces tert-butyl methyl ether (MTBE) as an additional product. MTBE can be produced either by dehydrating the tert-butanol formed from tert-butyl hydroperoxide in the propene epoxidation and reacting the resulting isobutene with methanol or by direct etherification of tert-butanol with methanol. Suitable processes for producing MTBE from isobutene and methanol are known from the prior art and are described in Ullmann's Encyclopedia of Industrial Chemistry, online edition, entry "Methyl Tert-Butyl Ether", pages 121-124, DOI 10.1002/14356007.a16_543.pub2. In another preferred embodiment, the hydroperoxide process uses ethylbenzene hydroperoxide and the integrated process produces styrene as an additional product.

In a further alternative, step a) uses hydrogen peroxide as the oxidant. Reacting propene with hydrogen peroxide to provide propylene oxide requires a catalyst which can be a homogeneous catalyst or a heterogeneous catalyst. Suitable homogeneous manganese complex catalysts for reacting propene with hydrogen peroxide to provide propylene oxide are known from WO 2011/106393. Preferably, a titanium zeolite catalyst is used as a heterogeneous catalyst and the reaction of propene with hydrogen peroxide is carried out in the presence of the titanium zeolite catalyst and a solvent. In a particularly preferred embodiment, the titanium zeolite catalyst comprises a titanium silicalite and the reaction is carried out in a methanol solvent, as described in Ullmann's Encyclopedia of Industrial Chemistry, online edition, entry "Propylene Oxide", pages 16-18, DOI 10.1002/14356007.a22_239.pub3 and WO 2017/089079. Alternatively, a titanium zeolite catalyst comprising a titanium MWW catalyst and an acetonitrile solvent can be used as described in WO 2004/099166, WO 2009/008493, WO 2015/010990 and WO 2015/010991.

In step b) of the existing process, a fraction of the propylene oxide provided in step a) is reacted with water to provide an aqueous glycol solution comprising monopropylene glycol and dipropylene glycol. The reaction is typically carried out in an adiabatic reactor at a molar ratio of propylene oxide to water of about 1:15 as described in Ullmann's Encyclopedia of Industrial Chemistry, online edition, entry "Propanediols", page 4, DOI 10.1002/14356007.a22_163.pub2. The fraction of the propylene oxide provided in step a) which is not reacted in step b) can be marketed or converted to other products, such as polyether polyols, at the same site.

In step c) of the existing process, monopropylene glycol and dipropylene glycol are separated by a multi-step distillation from the aqueous glycol solution provided in step b). The multi-step distillation typically comprises two to four distillation steps in series where water is separated as an overhead product followed by successive vacuum distillations which provide monopropylene glycol and dipropylene glycol as overhead products, as described in Ullmann's Encyclopedia of Industrial Chemistry, online edition, entry "Propanediols", page 4, DOI 10.1002/14356007.a22_163.pub2.

In the method of the invention, two steps d) and e) are added to the existing process which provide an aqueous phase comprising monopropylene glycol and dipropylene glycol in step e). This aqueous phase provided in step e) is passed to step c) of the existing process and replaces aqueous glycol solution provided by step b). At the same time the fraction of propylene oxide passed from step a) to step b) is reduced to lower the output of aqueous glycol solution from step b). Steps d) and e) may be added with a capacity where the aqueous phase provided in step e) can replace all of the aqueous glycol solution provided by step b). Step b) may then be operated at partial load or may be taken completely out of operation. Alternatively, steps d) and e) are added with a lower capacity where the aqueous phase provided in step e) can replace only a part of the aqueous glycol solution provided by step b). Step b) will then be operated at reduced load.

In step d) propene and hydrogen peroxide are reacted in the presence of a catalyst mixture comprising a phase transfer catalyst and a heteropolytungstate. This reaction is carried out in a liquid reaction mixture which comprises an aqueous phase with a maximum apparent pH of 6 and an organic phase.

Propene can be used in pure form or in a mixture with propane, wherein the proportion of propane may be up to 20 mol %. The proportion of propane in the propene used is preferably less than 5 mol %. Propene is preferably employed in a molar excess to hydrogen peroxide, preferably in a molar ratio of propene to hydrogen peroxide of from 1.1:1 to 10:1.

Hydrogen peroxide is preferably used in the form of an aqueous solution, preferably with a hydrogen peroxide content of 10 to 80% by weight, particularly preferably 30 to 70% by weight. Any commercially available grades of aqueous hydrogen peroxide solutions can be used. A crude hydrogen peroxide product obtained in the extraction stage of the anthraquinone process for producing hydrogen peroxide may also be used.

The catalyst mixture used in step d) comprises a heteropolytungstate. The heteroatom is preferably phosphorus or arsenic and is particularly preferably phosphorus, i.e. the heteropolytungstate is particularly preferably a polytungstophosphate. Heteropolytungstates are well known to a person skilled in the art. Preferred polytungstophosphates have a molar ratio of phosphorus to tungsten in the range of from 1:2 to 1:12. The polytungstophosphate can be generated in situ by combining phosphoric acid and sodium tungstate, which can be carried out in the liquid reaction mixture itself or prior to adding the polytungstophosphate to the liquid reaction mixture. Phosphoric acid and sodium tungstate are preferably employed at a molar ratio of phosphorus to tungsten in the range of from 1:2 to 10:1, preferably from 4:1 to 8:1. The polytungstophosphate reacts with hydrogen peroxide in the liquid reaction mixture to form peroxotungstates and peroxotungstophosphates, for example $PO_4[WO(O_2)_2]_4^{3-}$ and $HPO_4[WO(O_2)_2]_2^{2-}$ as well as partially protonated forms thereof, which are presumably the catalytically active species for oxidizing propene.

The catalyst mixture used in step d) also comprises a phase transfer catalyst. The phase transfer catalyst comprises a cation or a compound which forms a cation in the aqueous phase, whereby the cation can form a salt with a peroxotungstate or heteropolyperoxotungstate, which salt is soluble in the organic phase of the liquid reaction mixture. The phase transfer catalyst preferably comprises a singly-charged cation or a compound which forms a singly-charged cation in the aqueous phase. Suitable as phase transfer catalyst are tertiary amines, tertiary and quaternary ammonium salts, and quaternary phosphonium salts. Suitable counterions for tertiary and quaternary ammonium salts are the anions chloride, bromide, nitrate, sulphate, hydrogen phosphate, dihydrogen phosphate, methyl sulfonate, methyl sulphate and ethyl sulphate. The phase transfer catalyst is preferably used in an amount which results in a molar ratio in the liquid mixture of phase transfer catalyst to tungsten in the range of from 0.2:1 to 3:1 and particularly preferably of from 0.4:1 to 1:1, where the molar ratio refers to the cations or compounds forming cations in the employed phase transfer catalyst and to the employed amount of tungsten.

In a preferred embodiment, the phase transfer catalyst is a tertiary amine or a tertiary or a quaternary ammonium salt which comprises in total at least 12 carbon atoms, preferably from 12 to 60 carbon atoms. Preferred are tetraalkylammonium salts. Suitable tertiary amines are for example dodecyldimethylamine, hexadecyldimethylamine, octadecyldimethylamine, tributylamine and trioctylamine. Suitable tertiary ammonium salts are the protonation products of these teriary amines. Suitable quaternary ammonium salts are for example dodecyltrimethylammonium salts, hexadecyltrimethylammonium salts, octadecyltrimethylammonium salts, methyltributylammonium salts and methyltrioctylammonium salts. More preferably, the phase transfer catalyst comprises a tertiary or quaternary ammonium ion having the structure $R^1R^2R^3NR^{4+}$, wherein $R^1$, $R^2$ and $R^3$ are the same or different and are each selected from alkyl groups having from 8 to 10 carbon atoms and $R^4$ is hydrogen or methyl. Most preferably, the phase transfer catalyst comprises methyltri(octyl/decyl)ammonium methylsulfate (CAS No. 2387913-24-6).

In another preferred embodiment, the phase transfer catalyst comprises at least one salt having a tertiary or quaternary ammonium ion of the structure $R^1R^2R^3R^4N^+$, where $R^1$ is a $Y—O(C＝O)R^5$ group with Y being $CH_2CH_2$, $CH(CH_3)$ $CH_2$ or $CH_2CH(CH_3)$ and $R^5$ being an alkyl group or alkenyl group having 11 to 21 carbon atoms, $R^2$ is hydrogen or an alkyl group having 1 to 4 carbon atoms, and $R^3$ and $R^4$ are each independently $R^1$, an alkyl group having 1 to 4 carbon atoms or $Y—OH$. Preferred are quaternary ammonium salts with methylsulphate as the counterion, where $R^2$ is a methyl group and $R^5$ is a linear alkyl group or alkenyl group. Particularly preferred are the salts $(CH_3)_3N^+CH_2CH_2O(C＝O)R^5$ $CH_3OSO_3^-$, $(CH_3)_2N^+(CH_2CH_2OH)(CH_2CH_2O$ $(C＝O)R^5)$ $CH_3OSO_3^-$, $(CH_3)_2N^+(CH_2CH_2O(C＝O)$ $R^5)_2$ $CH_3OSO_3^-$, $CH_3N^+(CH_2CH_2OH)_2(CH_2CH_2O$ $(C＝O)R^5)$ $CH_3OSO_3^-$, $CH_3N^+(CH_2CH_2OH)$ $(CH_2CH_2O(C＝O)R^5)_2$ $CH_3OSO_3^-$, $CH_3N^+$ $(CH_2CH_2O(C＝O)R^5)_3$ $CH_3OSO_3^-$, $(CH_3)_3N^+CH_2CH$ $(CH_3)O(C＝O)R^5$ $CH_3OSO_3^-$, $(CH_3)_2N^+(CH_2CH$ $(CH_3)OH)(CH_2CH(CH_3)O(C＝O)R^5)$ $CH_3OSO_3^-$ and $(CH_3)_2N^+(CH_2CH(CH_3)O(C＝O)R^5)_2$ $CH_3OSO_3^-$, in which $R^5$ is in each case a linear alkyl group or alkenyl group having 11 to 21 carbon atoms. Most preferred is the salt $(CH_3)_2N^+(CH_2CH(CH_3)O(C＝O)R^5)_2$ $CH_3OSO_3^-$ in which $R^5$ is an alkyl group or alkenyl group having 11 to 17 carbon atoms. The phase transfer catalysts of this embodiment may be prepared by esterifying ethanolamine, isopropanolamine, diethanolamine, diisopropanolamine, triethanolamine or triisopropanolamine with a fatty acid and subsequent quaternization with dimethyl sulphate. These phase transfer catalysts have the advantage that they are readily biodegradable, unlike tetraalkylammonium salts, and can be introduced into a biological treatment plant without further pretreatment. The salts with methylsulphate as anion are also less corrosive than tetraalkylammonium halides.

The reaction of step d) is carried out in a liquid reaction mixture which comprises two liquid phases, an aqueous phase with a maximum apparent pH of 6 and an organic phase. The term "apparent pH" here refers to a value determined by measurement with a glass electrode employing a commercial pH meter calibrated with aqueous buffer solutions of known pH for measuring dilute aqueous solutions. This apparent pH differs from the notional pH, i.e. the negative logarithm of the hydrogen ion activity, by a constant value because the normal potential of the glass electrode in the aqueous phase of the reaction mixture, which comprises hydrogen peroxide and glycols, is different than the normal potential in pure water. The apparent pH of the aqueous phase is preferably maintained in the range from 1.0 to 3.5, particularly preferably in the range from 2.0 to 3.0. The apparent pH can be maintained in this range by addition of acid, preferably sulphuric acid or phosphoric acid, or by addition of base, preferably aqueous sodium hydroxide solution. Adjusting the apparent pH in the preferred range provides high selectivity for 1,2-propanediol and prevents enriching propene oxide in the aqueous phase, which simplifies the subsequent separation of propylene glycols from the aqueous phase.

The reaction is preferably conducted at a temperature in the range of from 50 to 110° C., more preferably 60 to 100° C. and particularly preferably 70 to 90° C. The reaction pressure is preferably higher than the vapour pressure of propene at the reaction temperature to ensure that most of the propene is present in the liquid organic phase of the liquid mixture.

The reaction of step d) can be carried out with or without addition of an organic solvent. The reaction is preferably conducted in the presence of at least one organic solvent having a boiling point of more than 100° C., preferably more than 120° C., which has a solubility in water of less than 250 mg/kg at 20° C. Suitable as solvents are alcohols having one or more hydroxyl groups, ethers, esters, ketones and alkylated aromatic hydrocarbons. Adding a solvent can improve extraction of a salt formed of the heteropolytungstate and the phase transfer catalyst into the organic phase. Preferably the amount of organic solvent is selected to provide a proportion of organic solvent in the organic phase during the reaction in the range of from 10 to 90 wt. %.

In a preferred embodiment, the organic solvent comprises an epoxidized fatty acid methyl ester. The epoxidized fatty acid methyl ester can be formed in situ in the reaction mixture of step d) by employing a fatty acid methyl ester with unsaturated fatty acid groups which reacts with hydrogen peroxide to the epoxidized fatty acid methyl ester. Particularly preferred are epoxidized fatty acid methyl esters which comprise fatty acid groups originating from vegetable oils, in particular soybean oil. The epoxidized fatty acid methyl esters have the advantage that they have low solubility in the aqueous phase.

In another preferred embodiment, the solvent comprises an alkylated aromatic hydrocarbon having 8 to 12 carbon atoms. Suitable alkylated aromatic hydrocarbons are, for example, 1,2-dimethylbenzene (o-xylene), 1,3-dimethylbenzene (m-xylene), 1,4-dimethylbenzene (p-xylene), ethylbenzene, 1,2,3-trimethylbenzene, 1,2,4-trimethylbenzene, 1,3,5-trimethylbenzene (mesitylene), 1-ethyl-2-methylbenzene, 1-ethyl-3-methylbenzene and 1-ethyl-4-methylbenzene and n-propylbenzene. Preferably, hydrocarbon mixtures comprising more than 50% by weight, particularly preferably more than 80% by weight, of alkylated aromatic hydrocarbons having 8 to 12 carbon atoms are used as solvent. The use of these solvents enables extracting most of the peroxotungstates into the organic phase of the reaction mixture and recycling them, which allows for operating the process without a need for recovering heteropolytungstate from the aqueous phase of the reaction mixture of step d). The phase transfer catalyst, the molar ratio of phase transfer catalyst to heteropolytungstate, the molar ratio of heteroatom of the heteropolytungstate to tungsten, the molar ratio of propene to hydrogen peroxide and the amount of solvent are then preferably selected to transfer as much as possible of the tungsten present in the liquid reaction mixture into the organic phase.

The phase transfer catalyst, the heteropolytungstate and the optionally used solvent can be added in step d) separately or in the form of mixtures containing two or all three of these components. Preferably, a solvent is used in step d) and the phase transfer catalyst and the heteropolytungstate are added dissolved in an organic phase comprising the solvent.

The reaction of step d) may be carried out in batch or continuously, with a continuous reaction being preferred. The concentration of hydrogen peroxide in the aqueous phase is preferably maintained in the range of 0.1 to 5% by weight, particularly preferably 0.5 to 3% by weight. The concentration of hydrogen peroxide can be adjusted in this range by appropriate selection of the reaction temperature, the molar ratio of propene to hydrogen peroxide and the residence time of the liquid mixture in the reactor in which the reaction takes place. The residence time of the reaction mixture is preferably adjusted to maintain a hydrogen peroxide conversion in the range of from 80 to 99%.

During the reaction, the liquid mixture is preferably mixed in order to generate a large phase interface between the aqueous phase and the organic phase. For this purpose, the reaction is preferably carried out continuously in a loop reactor which has fixed internals and the liquid mixture is passed through the loop reactor at a flow rate which generates a turbulent flow at the internals. Baffles, static mixing elements, structured packings or random packings can be used as internals for this purpose. In combination to these internals or as an alternative, heat exchangers, such as plate heat exchangers or tube bundle heat exchangers, may be used, in which turbulent flow is generated, for example between the plates of a plate heat exchanger or in the tubes of a tube bundle heat exchanger.

Preferably, all or a part of the reaction heat generated in step d) is removed while the reaction proceeds, preferably by cooling the reaction mixture in a heat exchanger. More preferably, the reaction is carried out continuously in a loop reactor which comprises a heat exchanger within the reactor loop for cooling the reaction mixture.

In step e) the liquid reaction mixture provided by step d) is separated into an organic phase, which is recycled to step d), and an aqueous phase, which comprises monopropylene glycol and dipropylene glycol and is passed to step c).

The separation of the two-phase reaction mixture provided by step d) is preferably carried out in a settler vessel. The two-phase reaction mixture is preferably passed through a coalescer element comprising a structured packing or a random packing with a surface wetted by the dispersed phase of the two-phase mixture in order to achieve a more complete separation.

The organic phase separated from the liquid reaction mixture provided by step d) may be recycled to step d) without further treatment. If the propene fed to step d) contains propane, it is preferred to separate a stream of unreacted propene from the organic phase in step e) before the organic phase is recycled to step d), with the separated stream of unreacted propene containing as much propane as the impure propene fed to step d). This way, an accumulation of propane in the organic phase of the reaction mixture of step d) can be avoided for a continuous reaction. The separated stream of unreacted propene is preferably passed to a C3 splitter for separating propene and propane and the recovered propene is recycled to step d) or passed as starting material to step a). If the existing integrated process for making propylene oxide and propylene glycol comprises a C3 splitter, the stream of unreacted propene separated in step e) can be passed to this C3 splitter.

In a preferred embodiment, the aqueous phase comprising monopropylene glycol and dipropylene glycol separated in step e) is subjected to a hydrogenation treatment before it is passed to step c). The hydrogenation is preferably carried out using a supported hydrogenation catalyst comprising one or more metals from the group of Ru, Rh, Pd, Pt, Ag, Ir, Fe, Cu, Ni and Co on a support, wherein activated carbon, $SiO_2$, $TiO_2$, $ZrO_2$, $Al_2O_3$ and aluminium silicates are preferred as support. Preference is given to hydrogenation catalysts comprising ruthenium as active metal. The catalytic hydrogenation is preferably carried out at a partial hydrogen pressure of 5 to 50 bar, preferably 5 to 35 bar, more preferred 7 to 30 bar, even more preferred 8 to 25 bar, and a temperature of 80° C. to 140° C., preferably 90° C. to 120° C. The hydrogenation catalyst may be used as a suspension or as a fixed bed, a trickle bed hydrogenation with a fixed bed catalyst being preferred. The hydrogenation can prevent problems caused by decomposition of hydrogen peroxide which has not reacted in step d) and enters the multi-step distillation of step c). The hydrogenation also converts the by-products 1-hydroperoxy-2-propanol, 2-hydroperoxy-1-propanol and hydroxyacetone formed in step d) to monopropylene glycol and thereby improves the yield of monopropylene glycol.

If the aqueous phase separated in step e) contains monopropylene glycol at a lower concentration than the aqueous glycol solution provided by step b) of the existing process, an additional distillation step, to which the aqueous phase separated in step e) and where water is separated as an overhead product, may be added to the process. If the process comprises a hydrogenation treatment as described in the preceding paragraph, this additional distillation step is carried out subsequent to the hydrogenation treatment. The additional distillation step is preferably operated to provide a bottoms product which can be separated with the multi-step distillation of the existing process without changes to the existing distillation equipment.

EXAMPLE

Preparation of Initial Epoxidation Catalyst Solution

A mixture of 100 g 70% by weight hydrogen peroxide, 155 g demineralized water, 160 g 85% by weight phosphoric acid and 100 g sodium tungstate dihydrate was stirred for 2 h at room temperature. Then, a solution of 150 g of methyltri (octyl/decyl)ammonium methylsulfate (CAS No. 2387913-24-6) in 1020 g Hydrosol A 200 ND (a mixture of C10 alkyl benzenes) was added and the mixture was stirred for another 2 h at room temperature. The aqueous and organic phases were then separated to provide 1230 g of organic phase as initial epoxidation catalyst solution.

Reaction of Propene With Hydrogen Peroxide

The reaction of propene with hydrogen peroxide was carried out at a temperature of 80° C. and a pressure of 30 bar in a loop reactor with a loop volume of 0.45 l, a circulation pump and a heat exchanger for adjusting the reaction temperature, which was operated at a circulation rate of 130 kg h$^{-1}$. The reactor was equipped with a catalyst feed reservoir, an organic phase collection vessel equipped with a stirrer, and feed pumps for feeding liquid propene, liquid propane, an aqueous hydrogen peroxide solution and liquid from the catalyst feed reservoir. The initial epoxidation catalyst solution was charged to the catalyst feed reservoir and a mixture of 100 g 70% by weight hydrogen peroxide, 155 g demineralized water, 160 g 85% by weight phosphoric acid and 20 g sodium tungstate dihydrate was charged to the organic phase collection vessel. The loop initially contained reaction mixture from a previous experiment. Circulation was started and maintained at 130 kg h$^{-1}$ and the circulating mixture was heated to 80° C. Then 80 g h$^{-1}$ of propene, 50 g h$^{-1}$ of propane, 210 g h$^{-1}$ of a 15% by weight hydrogen peroxide solution containing 0.1% by weight phosphoric acid, and 320 g h$^{-1}$ of organic catalyst solution from the catalyst feed reservoir were introduced into the loop reactor, cooling the circulating mixture to maintain a reaction temperature of 80° C. A two-phase oxidation reaction mixture was removed from the loop reactor in an amount corresponding to the amounts added and 18 g h$^{-1}$ of a 9% by weight aqueous disodium sulfate solution was added to this mixture at the reactor outlet to speed up phase separation. The organic phase and the aqueous phase of the resulting mixture were separated, and the organic phase was passed to the organic phase collection vessel after depressurizing and cooling to 25° C. When 500 g of the organic phase had accumulated in the organic phase collection vessel, the content of the vessel was thoroughly mixed by stirring for 5 min, phases were separated by settling and the organic phase was passed to the catalyst feed reservoir with the aqueous phase remaining in the organic phase collection vessel. After about 11 h of operation, the feeding of reactants and the circulation in the loop reactor were stopped and 0.33 g of sodium tungstate dihydrate were charged to the organic phase collection vessel to compensate for losses. The next day, circulation in the loop reactor was restarted, dosing of reactants was resumed after the reaction temperature had been established in the loop reactor and the reaction was continued for another 11 h. The aqueous phase separated from the oxidation reaction mixture was analyzed for hydrogen peroxide by redox titration and for organic products by capillary GC (25 m CP-WAX-52 CB column from Agilent, He carrier gas, temperature program starting at 50° C. with ramps of 20 K/min to 90° C., 10 K/min to 220° C. and 5 K/min to 235° C., FID detector) and $^{1}$H-NMR and contained 0.2% by weight hydrogen peroxide, 18.3% by weight monopropylene glycol, 2.3% by weight dipropylene glycol, 0.2% by weight tripropylene glycol, 0.2% by weight hydroxyacetone and 0.1% by weight acetic acid after a steady state operation was reached.

The aqueous solution thus obtained can be separated with the distillation sequence typically used for separating a reaction mixture obtained by acid catalyzed adiabatic hydro-lysis of propylene oxide, preferably after catalytic hydroge-nation of the peroxides which also converts byproduct hydroxyacetone to product monopropylene glycol.

The invention claimed is:

1. A method for increasing propylene oxide output of an existing integrated process for making propylene oxide and propylene glycol, said integrated process comprising
   a) reacting propene with an oxidant to provide the pro-pylene oxide,
   b) reacting a fraction of the propylene oxide provided in a) with water to provide an aqueous glycol solution comprising monopropylene glycol and dipropylene glycol, and
   c) separating the monopropylene glycol and the dipropyl-ene glycol from said aqueous glycol solution by a multi-step distillation,
   said method comprising:
   d) reacting propene and hydrogen peroxide in the pres-ence of a catalyst mixture, comprising a phase transfer catalyst and a heteropolytungstate, in a liquid reaction mixture comprising an aqueous phase with a maximum apparent pH of 6 and an organic phase, wherein appar-ent pH refers to a value determined by measurement with a glass electrode employing a commercial pH meter calibrated with aqueous buffer solution of known pH for measuring dilute aqueous solutions, and
   e) separating the liquid reaction mixture provided by d) into a further organic phase, which is recycled to d), and a further aqueous phase comprising monopropyl-ene glycol and dipropylene glycol, which is passed to c),
   wherein said further aqueous phase provided by e) replaces the aqueous glycol solution provided by b), and at the same time reduces a fraction of the propylene oxide passed from a) to b) to lower an output of the aqueous glycol solution from b).

2. The method of claim 1, wherein the oxidant in a) is tert-butyl hydroperoxide, and the integrated process pro-duces tert-butyl methyl ether as an additional product.

3. The method of claim 1, wherein the oxidant in a) is ethylbenzene hydroperoxide, and the integrated process produces styrene as an additional product.

4. The method of claim 1, wherein the oxidant in a) is hydrogen peroxide, and the reaction of the propene with the hydrogen peroxide is carried out in the presence of a titanium zeolite catalyst and a solvent.

5. The method of claim 1, wherein the further aqueous phase comprising monopropylene glycol and dipropylene glycol separated in e) is subjected to a hydrogenation treatment before being passed to c).

* * * * *